United States Patent [19]

Cherkin et al.

[11] Patent Number: 4,647,591

[45] Date of Patent: Mar. 3, 1987

[54] METHOD FOR IMPROVING MEMORY

[75] Inventors: Arthur Cherkin; James F. Flood, both of Los Angeles, Calif.; David T. Wong, Indianapolis, Ind.

[73] Assignee: Eli Lilly and Company, Indianapolis, Ind.

[21] Appl. No.: 785,411

[22] Filed: Oct. 7, 1985

[51] Int. Cl.⁴ .......................................... A61K 31/195
[52] U.S. Cl. .................................................. 514/651
[58] Field of Search ........................................ 514/651

[56] References Cited

PUBLICATIONS

Altman et al., Psychopharmacology, 84, 496-502 (1984).
Broekkamp et al., Pharm. Biochem. Behav., 13, 643-646 (1980).
deWied et al., Life Sciences, 31, 709-719 (1982).
Lorden et al., Pharmacol Biochem Behav., 17, 435-443 (1982).
Garrigon et al., Psychopharm, 74, 66-70 (1981).
Cherkin et al., 14th Annual Meeting, Society for Neuroscience, Talk 74, 15, Thursday, Oct. 11, 1984.

Primary Examiner—Stanley J. Friedman
Attorney, Agent, or Firm—Charles W. Ashbrook; Leroy Whitaker

[57] ABSTRACT

Fluoxetine can be employed to improve memory in mammals and to treat amnesia.

4 Claims, No Drawings

METHOD FOR IMPROVING MEMORY

BACKGROUND OF THE INVENTION

This invention relates to a method for improving memory employing fluoxetine.

Fluoxetine is the generic name given to 3-(4-trifluoromethylphenoxy)-N-methyl-3-phenylpropylamine. The compound is described in U.S. Pat. No. 4,314,081. Fluoxetine is useful in the treatment of depression (U.S. Pat. No. 4,018,895), hypertension (U.S. Pat. No. 4,329,356), and also is said to be useful in causing and promoting analgesia (see U.S. Pat. Nos. 4,035,511 and 4,083,982).

We have now discovered that fluoxetine is also useful for improving memory retention and treating amnesia.

SUMMARY OF THE INVENTION

This invention provides a method for treating amnesia and for improving memory retention in mammals, comprising administering to a mammal an effective dose of fluoxetine or a pharmaceutically acceptable salt thereof. A preferred salt is one formed by reacting fluoxetine with a mineral acid such as hydrochloric acid or sulfuric acid.

DETAILED DESCRIPTION OF THE INVENTION

The method of this invention is practiced by administering a pharmaceutical formulation of fluoxetine, preferably fluoxetine hydrochloride, to a mammal. Formulations of fluoxetine and its salts are already known in the art and are described in detail in U.S. Pat. No. 4,194,009. As used herein "fluoxetine" includes the free base and its pharmaceutically acceptable acid addition salts.

Fluoxetine may be administered by any number of routes, including oral, transdermal, subcutaneous, intravenous, intramuscular, inhalation and the like. The compound will normally be administered via the oral route.

Fluoxetine is effective over a wide dosage range. Normal daily doses effective to enhance memory retention or to treat amnesia will be from about 0.5 to about 100 mg/kg of animal body weight. In the treatment of adult humans, the range of about 1 to about 50 mg/kg, in single or divided doses, will normally be employed. It will of course be recognized that the specific dosage regimen to be followed in an individual case will be dictated by a physician or other medical attendant, in light of relevant circumstances including the subject to be treated, the degree of improved memory retention desired, the severity of the amnesia to be treated, the route of administration and similar related factors.

We have discovered that fluoxetine is effective in improving the retention of memory in mammals. The compound can be employed in the treatment of amnesia. Fluoxetine appears to be a unique chemical substance in that it exhibits a relatively high degree of specificity in blocking serotonin uptake without significantly affecting the uptake of dopamine or norepinephrine. Fluoxetine also does not bind to dopamine, acetylchlorine, GABA, histamine, opiate or benzodiazepine receptors.

Several agents have been demonstrated to improve memory. The most notable agents include nicotine, caffeine, amphetamine, strychnine and picrotoxin. Many of these agents cause adverse affects to such extent that their routine use is not possible. Fluoxetine, on the other hand, has few adverse side effects and consequently can be used chronically.

Several tests were carried out to establish the memory enhancing effects caused by fluoxetine. Male mice obtained from Charles River Breeding Laboratories, Wilmington, MA, were employed for the tests. The animals were individually caged 24–48 hours prior to training and remained singly housed until retention was tested one week later. The mice were trained on a T-maze active avoidance task between 0700 and 1500 hours. Fluoxetine hydrochloride was dissolved in 70 $\mu$l of 95% alcohol and sufficient distilled water to prepare the desired dilution.

The T-maze consisted of a black plastic start alley with a start box at one end and two goal boxes at the other; a brass rod floor ran throughout the maze. Each goal box was fitted with a slotted plastic liner (the bottom of which went below the shock grid) which was used to remove the mice from the goal box without hand contact. The start box was separated from the start alley by a plastic guillotine door which prevented the mouse from moving down the alley until the training started. The intertrial interval was 30 s with a muffled doorbell-type buzzer as the conditioned stimulus and footshock set at 0.30 ma.

Mice were not permitted to explore the maze before training. A training trial started when a mouse was placed into the start box. The guillotine door was raised and the buzzer sounded simultaneously, then 5 s later footshock was applied. The goal box that the mouse first entered on this trial was designated as "incorrect" and the footshock was continued until the mouse entered the other goal box, which on all seubsequent trials was designated "correct" for the particular mouse. At the end of each trial, the mouse was removed from the goal box by lifting the plastic liner and the mouse was carefully returned to its home cage. A new trial began by placing the mouse in the start box, sounding the buzzer and raising the guillotine door, with footshock beginning 5 s later if the mouse did not move into its correct goal box.

As training proceeded, a mouse made one of two types of responses. A response latency longer than 5 s was classed as an escape from the footshock. A response latency less than or equal to 5 s was considered an avoidance, since the mouse avoided receiving a footshock. Two exclusion criteria were applied to reduce learning variability among mice, as follows. On the first training trials, mice with escape latencies greater than 20 s were discarded. Mice not having at least one errorless escape latency between 1.5 and 3.5 s on training trials 2 or 3 were excluded. The total exclusions were fewer than 20%. Mice received a 0.35 ml subcutaneous injection of the vehicle or freshly prepared drug solution within 2 minutes after training. All solutions were blind-coded to eliminate experimenter bias.

One week after training and drug administration, the T-maze training was resumed until the mice made 5 avoidance responses in 6 consecutive training trials. Two parametric measures of memory retention were analyzed. The first measure is the mean number of trials to the first avoidance response for all mice within a group. The second measure was the mean number of trials to reach the 5 out of 6 criterion. The overall significance of the drug treatment effect was determined by a one-way analysis of variance. Dunnett's t-test was used to make multiple comparisons between each drug group and the control group.

A non-parametric measure of retention was derived to better visualize the effects of drug treatments on retention test performance and to correspond with usual reporting practice. For this, the number of trials to the first avoidance response was dichotomized to yield a percent recall score. Those mice making their first avoidance in three trials or less were classed as remembering the original training. This criterion was adopted because it has provided optimal separation between the retention test performance of naive mice (with no T-maze training) and well-trained mice.

The procedure for training and testing mice for passive avoidance employs an apparatus consisting of a black start compartment joined to a white shock compartment by a partition containing a hole through which the mice could enter the white compartment. In the white compartment, footshock was given until the mouse returned to the black compartment. Acquisition of this task is determined by the latency-to-enter and latency-to-escape from the shock compartment and by the footshock intensity. To reduce individual differences in acquisition, only mice with latencies of 1.5–3.4 s to enter and to escape from the shock compartment were used; other mice were discarded. Less than 15% of the mice were discarded. The footshock intensity, used to contorl overall training strength, was set at 0.20 ma sb that control mice would show poor recall on the retention test one week after training. In order to test retention, the mice were again placed into the black compartment and the latency-to-enter the white compartment was taken as a measure of retention. Mice not entering the white compartment within 180 s were removed and the test was terminated. A latency-to-enter the white shock compartment on the test day of 20 s or less was defined as amnesia, as this represents the maximum latency-to-enter of naive mice. Training and testing were done between 0900 and 1400 h.

EXPERIMENT 1

Effect of Post-Training Subcutaneous Administration of Fluoxetine on Memory Retention Most drugs that are recognized as having the ability to improve memory retention do so when administered shortly after training. The purpose of this experiment was to determine the range of doses over which FLU improved retention (70% or greater recall score) compared to controls (25% recall score). The mice were trained in a T-maze as described above and received 1 of 4 doses of fluoxetine hydrochloride (2.5, 5, 10 or 15 mg/kg, s.c.), or vehicle, within 2 minutes after training. The N per group was 20. The mice were tested one week after training and drug administration as described above.

Results

As intended, the retention test performance of the vehicle control group was poor, with only 20% recall. An analysis by ANOVA of mean trials to first avoidance indicated a significant effect of fluoxetine on memory retention ($F=9.11$, $df=4,95$; $P<0.001$). A further analysis of either mean trials to first avoidance response or to criterion using Dunnett's t-test showed that 2.5 mg/kg had no significant effect on retention, but 5, 10 and 15 mg/kg improved retention by either measure ($P<0.05$, $P<0.01$, $P<0.01$ respectively).

EXPERIMENT 2

Effect of Post-Training Intracerebroventricular Administration of Fluoxetine on Memory Retention The purpose of Experiment 2 was to test if fluoxetine can affect memory processing by acting directly on the central nervous system. Mice were trained as in Experiment 1. Twenty-four to forty-eight h prior to training a single hole was drilled over the third ventricle ($-0.5$ mm relative to bregma, 0.5 right of the central suture) while mice were in a stereotaxic instrument under methoxyflurane (Metofane) anesthesia. Within 3 minutes after training, mice were anesthetized with enflurane, and received one of 5 doses of fluoxetine in 2 $\mu$l of the vehicle or of the vehicle alone. The doses of fluoxetine per mouse were: 4, 8, 16, 20 and 24 $\mu$g. The N per group was 20. The mice were tested one week after training.

Results

The vehicle control group showed poor retention (20% recall score). The ANOVA yielded a significant drug effect for mean trials to first avoidance response ($F=3.14$, $df=5,114$; $P<0.01$) as well as mean trials to criterion ($F=3.08$, $df=5,114$; $P<0.025$). A further analysis of the data by Dunnett's t-test on mean trials either to first avoidance response or to criterion showed that groups receiving fluoxetine had significantly improved recall score at 8 $\mu$g and 16 $\mu$g ($P<0.051$) but 20 $\mu$g and 24 $\mu$g were optimal ($P<0.01$).

EXPERIMENT 3

Effect of Pre-training Subcutaneous Administration of Fluoxetine on Memory Retention Drugs which improve retention when administered after training generally do so at a lower dose when administered prior to training. To determine if this is also true for fluoxetine, we administered 0.25, 0.5, 1.0, 2.5, 5.0, 10.0 mg/kg, or the vehicle, 1 h prior to training. The mice were trained as i Experiment 1. The N per group was 20. The retention test was given one week after training.

Results

The ANOVA for mean trials to first avoidance response yielded a significant drug effect ($F=6.59$, $df=6,133$; $P<0.001$) as well as the trials to criterion ($F=8.24$, $df=6,133$; $P<0.001$). Analysis of either mean trials to first avoidance response or to criterion indicated that fluoxetine at 0.25 mg/kg did not significantly affect recall score compared to the control group. The group receiving fluoxetine at 0.5 mg/kg differed significantly from the control by either measure of retention ($P<0.05$). Fluoxetine at 1.0, 2.5 and 5.0 mg/kg differed significantly from the control group at $P<0.01$. Fluoxetine between 1.0 and 5.0 mg/kg had the highest recall scores (75–80%), while 10 mg/kg was less facilitating (50% recall score). The amnestic effect in the fluoxetine 10.0 mg/kg group was not significant.

EXPERIMENT 4

Dose-Response Improvement of Recall Score by Pre-Test Administration of Fluoxetine The purpose of Experiment 3 was to test if fluoxetine improved recall of information poorly stored in memory because of weak training. The mice were trained as in Experiment 1. One h before the 1-week retention test, mice were injected subcutaneously with 2.5 mg/kg of fluoxetine which facilitated retention when fluoxetine was injected prior to training (Experiment 3) or with the vehicle. The N per group was 15.

Results

The controls performed poorly on the retention test as intended, with only 13% recall or 9.13±1.51 trials to criterion. The fluoxetine-injected group showed improved retention test performance with a recall score of 80% or 6.87±0.99 trials to criterion. An ANOVA showed that the difference between groups was significant by mean trials either to the first avoidance ($F=24.93$, $df=1,28$; $P<0.001$) or to criterion ($F=23.73$, $df=1,28$; $P<0.001$).

EXPERIMENT 5

Effect of Fluoxetine on Acquisition

Administration of a drug prior to training (Experiment 3) or prior to testing (Experiment 4) could have resulted from improved acquisition rather than from enhanced memory processing. To determine if this occurred, we tested the effect of fluoxetines on acquisition of T-maze active avoidance. Fluoxetine at 0.5, 1, 2.5, 5, 10, 20, 25, 30 or 35 mg/kg, or the vehicle, was administered subcutaneously 1 h prior to training. The mice were trained as in Experiment 1 except that training continued until 5 avoidances were made in 6 consecutive trials. Mice not reaching criterion in 15 training trials were given a score of 15. The N per group was 10.

Results

The mean trials to the avoidance criterion for the vehicle control group was 10.4. The fluoxetine-injected groups between 1 and 20 mg/kg where all mice reached the criterion had mean trials to criterion ranging from 9.9 to 11.0 and none were significantly different from the control mean.

EXPERIMENT 6

Time-Dependent Improvement of Memory Retention by Post-Training Subcutaneous Administraton of Fluoxetine Drugs which are recognized as improving memory retention show a decline in effectiveness as the time from the end of training until the drug is administered increases. The purpose of Experiment 6 was to determine if fluoxetine showed a time-dependent facilitation of retention. Separate groups of mice received a single injection of fluoxetine (15 mg/kg, s.c.) 0, 30, 60 or 90 minutes after training. Two control groups received injections of the vehicle 0 or 90 minutes after training. The N per group was 10. Retention was tested 1 week after training.

Results

The results indicated that fluoxetine yielded a time-dependent facilitation of retention. The ANOVA for the drug effect was significant for mean trials to first avoidance ($F=3.75$, $df=5,54$; $P<0.01$) and for mean trials to criterion ($F=3.93$, $df=5,54$; $P<0.01$). Comparisons with the control group (0 or 90 minutes) using Dunnett's t-test yielded significantly lower mean trials to first avoidance response, and lower mean trials to criterion for fluoxetine administered at 0 or 30 minutes ($P<0.01$) and at 60 minutes ($P<0.05$). Fluoxetine injected 90 minutes after training did not significantly affect retention by either measure.

EXPERIMENT 7

Anti-Amnestic Effect of Fluoxetine

Amnesia caused by inhibitors of brain protein synthesis can be blocked by a variety of neurotransmitter agonists and hormones. The purpose of Experiment 7 was to determine if fluoxetine had anti-amnestic properties against both anisomycin (ANI), a protein synthesis inhibitor, and scopolamine (SCO), and acetylcholine receptor blocker.

The training conditions in this experiment were altered to assure that control mice would have high recall scores (70–80%) in order to permit detecting amnesia caused by ANI or SCO. To accomplish this, the nominal footshock level was increased from 0.30 to 0.35 ma, the buzzer was loud rather than muffled, and the intertrial interval was 45 s instead of 30 s. The experiment was done in two parts because of the different experimental conditions under which ANI and SCO must be used. Retention was tested one week after training. Because the amnestic effects of ANI and SCO are robust, the N per group was 10.

ANISOMYCIN STUDY

In this study, ANI (20 mg/kg) or vehicle was injected subcutaneously 15 minutes prior to training, fluoxetine (15 mg/kg) or the vehicle was injected immediately after training, then a second injection of ANI or vehicle was given 1.75 h after training. The two injections of ANI inhibit protein synthesis in the brain for 4–6 h. The three groups were A(V)A, A(F)A, and V(V)V, where A=ANI, F=fluoxetine and V=vehicle. The results yielded a control group [V(V)V] with good retention (73% recall score). ANI(V)ANI treatment induced amnesia (13% recall score). The ANI(F)ANI group had a recall score of 80%, indicating that fluoxetine counteracted the amnesia. An ANOVA indicated a significant drug effect for mean trials either to first avoidance ($F11.38$, $df=2,27$; $P<0.001$) or to criterion ($F13.83$, $df=2,27$; $P<0.001$). A comparison by either measure of retention indicated that A(F)A differed significantly from A(V)A ($P<0.01$) but not from V(V)V.

SCOPOLAMINE STUDY

In the second study, SCO (1 mg/kg) or saline was injected immediately after training and fluoxetine (15 mg/kg) or the vehicle was administered 45 minutes later. Three groups were used: SCO(V), SCO(F) AND V(V), abbreviations as above. The results indicated that the V(V) group remembered well, with 80% recall score. SCO(V) induced amnesia (10% recall score. The group that received SCO plus fluoxetin [SCO(F)] had a recall score of 70%, indicating the fluoxetin counteracted scopolamine-induced amnesia. An ANOVA indicated a significant drug effect for mean trials either to first avoidance ($F16.00$, $df=2,27$; $P<0.001$) or to criterion ($F14.13$, $df=2,27$; $P<0.001$). An analysis of mean trials to first avoidance and of mean trials to criterion yielded a significant difference ($P<0.01$) between SCO(V) and SCO(F).

EXPERIMENT 8

Effect of Fluoxetine on Retention for Passive Avoidance Conditioning

Drugs that enhance memory retention usually improve retention in passive avoidance as well as active avoidance paradigms. The purpose of Experiment 8 was to determine if fluoxetine would improve retention for one-trial passive avoidance. The mice were trained as described above. They were injected within 2 minutes after training with 5, 10, 15, 20, or 25 mg/kg of fluoxetine or the vehicle. The N per group was 15. The retention test was given one week after training. The percent mice showing passive avoidance in the control group was low (20%). Fluoxetine improved retention test scores optimally at 15 mg/kg yielding 73% of the mice showing passive avoidance. The difference between the control and fluoxetine at 15 mg/kg was significant ($P=0.004$).

The results of the foregoing evaluations demonstrate fluoxetine and its salts are effective in improving memory retention and in treating amnesia.

We claim:

1. A method for improving memory in mammals comprising administering to a mammal in need of memory improvement fluoxetine or a pharmaceutically acceptable salt thereof at a dose effective for improving memory.

2. The method of claim 1 wherein fluoxetine hydrochloride is administered to humans.

3. A method for treating amnesia comprising administering to a subject in need of treatment an anti-amnestic amount of fluoxetine or a pharmaceutically acceptable salt thereof.

4. The method of claim 3 wherein fluoxetine hydrochloride is administered to humans.

* * * * *